(12) United States Patent
Orth et al.

(10) Patent No.: US 12,070,543 B2
(45) Date of Patent: Aug. 27, 2024

(54) BLOOD PROCESSING APPARATUS AND METHOD FOR DETOXIFYING BACTERIAL LIPOPOLYSACCHARIDE IN VIVO

(71) Applicant: Orth Consulting, LLC, Maineville, OH (US)

(72) Inventors: Donald S. Orth, Cincinnati, OH (US); Roger W. Orth, Cincinnati, OH (US)

(73) Assignee: Orth Consulting, LLC, Maineville, OH (US)

( * ) Notice: Subject to any disclaimer, the term of this patent is extended or adjusted under 35 U.S.C. 154(b) by 0 days.

(21) Appl. No.: 18/323,055

(22) Filed: May 24, 2023

(65) Prior Publication Data

US 2023/0414855 A1  Dec. 28, 2023

Related U.S. Application Data

(60) Provisional application No. 63/345,779, filed on May 25, 2022.

(51) Int. Cl.
*A61M 1/36* (2006.01)
*A61F 2/01* (2006.01)
(Continued)

(52) U.S. Cl.
CPC ............ *A61M 1/3687* (2013.01); *A61F 2/01* (2013.01); *A61F 2/95* (2013.01); *A61K 8/66* (2013.01);
(Continued)

(58) Field of Classification Search
CPC ............ A61M 1/15632; A61M 1/1621; A61M 1/267; A61M 1/3489; A61M 1/36; A61M 1/3621; A61M 1/3653; A61M 1/3679; A61M 1/3687; A61M 1/3689; A61M 25/00; A61M 2202/0445; A61M 2202/0456; A61M 2202/046; A61M 2202/07; A61M 2202/203; A61M 2202/206; A61M 2205/3303; B01D 15/00; B01D 15/08; B01D 63/02; B01D 63/06; B01D 69/04; B01D 69/043; B01D 69/08; B01J 20/22; B01J 31/003; B01J 2220/48;
(Continued)

(56) References Cited

U.S. PATENT DOCUMENTS

| 10,881,781 B1 * | 1/2021 | Orth ........................ C12Q 1/42 |
| 11,103,628 B1 * | 8/2021 | Orth .................... A61M 1/3679 |
| 11,305,045 B2 * | 4/2022 | Orth .................... A61M 1/3679 |

* cited by examiner

*Primary Examiner* — John Kim
(74) *Attorney, Agent, or Firm* — David R. Stevens; Stevens Law Group

(57) ABSTRACT

A detoxification method for treating sepsis, microbial infections, and other inflammatory conditions includes the steps of inducing flow of patient blood through a blood treatment device consisting of a bioreactor inlet and outlet in fluid connection to the circulatory system of a patient. Biological agents including lipopolysaccharide (LPS) and extracellular adenosine triphosphate (ATP) contained within patient blood can be irreversibly detoxified by passage of patient blood over a bioreactor surface having attached or immobilized alkaline phosphatase enzymes and acyloxyacyl hydrolase enzyme, with the bioreactor being contained within the blood treatment device. The method uses continuous treatment of a patient's blood to convert LPS and extracellular ATP in blood into inhibitors of inflammation in vivo without adding any chemicals to the bloodstream of the patient.

17 Claims, 5 Drawing Sheets

(51) Int. Cl.

| | | |
|---|---|---|
| *A61F 2/95* | (2013.01) | |
| *A61K 8/66* | (2006.01) | |
| *A61M 1/14* | (2006.01) | |
| *A61M 1/16* | (2006.01) | |
| *A61M 1/26* | (2006.01) | |
| *A61M 1/34* | (2006.01) | |
| *B01D 15/00* | (2006.01) | |
| *B01D 15/08* | (2006.01) | |
| *B01D 63/02* | (2006.01) | |
| *B01D 63/06* | (2006.01) | |
| *B01D 69/04* | (2006.01) | |
| *B01D 69/08* | (2006.01) | |
| *B01J 20/22* | (2006.01) | |
| *B01J 31/00* | (2006.01) | |
| *C07K 16/00* | (2006.01) | |
| *C07K 16/38* | (2006.01) | |
| *C07K 16/40* | (2006.01) | |
| *C12N 11/00* | (2006.01) | |
| *C12N 11/02* | (2006.01) | |
| *C12N 11/06* | (2006.01) | |
| *C12N 11/14* | (2006.01) | |
| *C12N 11/16* | (2006.01) | |
| *C12N 11/18* | (2006.01) | |
| *A61F 2/00* | (2006.01) | |

(52) U.S. Cl.
CPC ...... *A61M 1/15632* (2022.05); *A61M 1/1621* (2014.02); *A61M 1/267* (2014.02); *A61M 1/3489* (2014.02); *A61M 1/36* (2013.01); *A61M 1/3621* (2013.01); *A61M 1/3653* (2013.01); *A61M 1/3679* (2013.01); *A61M 1/3689* (2014.02); *B01D 15/00* (2013.01); *B01D 15/08* (2013.01); *B01D 63/02* (2013.01); *B01D 63/06* (2013.01); *B01D 69/04* (2013.01); *B01D 69/043* (2013.01); *B01D 69/08* (2013.01); *B01J 20/22* (2013.01); *B01J 31/003* (2013.01); *C07K 16/00* (2013.01); *C07K 16/38* (2013.01); *C07K 16/40* (2013.01); *C12N 11/00* (2013.01); *C12N 11/02* (2013.01); *C12N 11/06* (2013.01); *C12N 11/14* (2013.01); *C12N 11/16* (2013.01); *C12N 11/18* (2013.01); *A61F 2/00* (2013.01); *A61M 2202/0445* (2013.01); *A61M 2202/0456* (2013.01); *A61M 2202/046* (2013.01); *A61M 2202/07* (2013.01); *A61M 2202/203* (2013.01); *A61M 2202/206* (2013.01); *A61M 2205/3303* (2013.01); *B01J 2220/4812* (2013.01); *B01J 2220/4868* (2013.01)

(58) Field of Classification Search
CPC .. B01J 2220/4868; C07K 16/00; C07K 16/38; C07K 16/40; C12N 11/00; C12N 11/02; C12N 11/06; C12N 11/14; C12N 11/16; C12N 11/18; A61F 2/00; A61F 2/01; A61F 2/95; A61K 8/66
See application file for complete search history.

BLOOD PROCESSING APPARATUS AND METHOD FOR DETOXIFYING BACTERIAL LIPOPOLYSACCHARIDE IN VIVO

CROSS-REFERENCE TO RELATED APPLICATIONS

This application claims the benefit of U.S. Provisional Patent Application Ser. No. 63/345,779, filed May 25, 2022, which is hereby incorporated herein by reference in its entirety.

FIELD OF THE INVENTION

This invention relates to detoxifying Gram negative bacterial lipopolysaccharide (LPS) and other inflammatory compounds in a person's blood. More particularly, indwelling and extracorporeal bioreactors containing alkaline phosphatase and acyloxyacyl hydrolase enzymes enable conversion of LPS and proinflammatory compounds in blood into inhibitors of inflammation in vivo, without adding any chemicals to the bloodstream of a patient with sepsis, are described.

BACKGROUND OF THE INVENTION

Gram negative bacteria are common in the environment and in the gastrointestinal tract of many animal species and man. These bacteria have a cell wall surrounded by an outer membrane, or endotoxin, which is composed of lipopolysaccharide (LPS). LPSs are large molecules consisting of a lipid and a polysaccharide that constitutes the O-antigen, an outer and inner protein core joined by a covalent bond, and a lipid A moiety joined to the inner protein core by phosphate groups. The endotoxins produced by different Gram negative bacteria differ in their antigenicity due to differences in the O-antigen, but they all have the same biological effects which are mainly due to lipid A. Lipid A contains two phosphate groups that are believed to be essential for its toxicity. Endotoxins can be very harmful once they translocate from the intestinal tract into the bloodstream because as little as 10 picograms can cause inflammation and sepsis. Alkaline phosphatase (AP) can dephosphorylate LPS to detoxify and neutralize it.

Microbial infections are the primary cause of sepsis and sepsis-related mortality. The body responds to a microbial infection and LPS by releasing inflammatory substances into the bloodstream to up-regulate the immune system to fight the infection. This may lead to sepsis, which is a life-threatening condition that develops when the body's response to infection causes injury to its own tissues and organs. Sepsis may progress to toxic shock, which occurs when the body has an overwhelming response to infection—often referred to as a "cytokine storm"—that causes the blood pressure to drop to dangerously low levels and triggers damaging changes to the organs causing them to become dysfunctional and stop working, which results in death. One-in-four cases of sepsis in hospitals and one-in-two cases in intensive care units (ICUs) result from health care-associated infections, and antimicrobial resistance makes case management more difficult.

The World Health Organization (WHO) 2020 *Global Report on the Epidemiology and Burden of Sepsis* report estimated that sepsis affected an estimated 49 million people and was related to about 11 million preventable deaths worldwide in 2017. The Center for Disease Control (CDC) 2018 data estimated over 1.7 million cases of sepsis occur annually causing nearly 270,000 deaths and being responsible for 1 out of every 3 hospital deaths in the United States.

Sepsis ranked second (behind heart failure) as a condition with the highest 30-day readmission rates among Medicare patients, and many sepsis survivors face long-term physical challenges, cognitive impairment, and mental disorders. Sepsis costs billions of dollars every year and is among the most expensive condition treated in hospitals in the United States. The costs and burden on the health care system are staggering in light of the fact that sepsis may be prevented if symptoms are recognized early enough and treated appropriately.

Immediate, intensive treatment is crucial for surviving sepsis and preventing septic shock because the risk of death from sepsis and septic shock increases with every passing hour. Current treatment strategies include fluid replacement, antibiotics to control the infection, vasopressors to maintain adequate blood pressure, corticosteroids, and anti-inflammatory drugs to lessen inflammation, and insulin to stabilize blood sugar levels. In some cases, a person might require surgery to remove abscesses and necrotic tissues that are a source of the microbial infection and toxins. Many studies have reported intravenous (IV) treatment of sepsis and microbial infections with antibodies and alkaline phosphatases (APs).

AP (Enzyme Classification 3.1.3.1) is an enzyme present in all tissues in the body. AP has broad substrate specificities, which means that it removes phosphate from many kinds of molecules. In addition to detoxification of bacterial pathogens, intestinal AP (IAP) dephosphorylates LPS, flagellin, fragments of deoxyribonucleic acid (DNA) and synthetic single-stranded oligodeoxynucleotides that contain CpG DNA (e.g., a cytosine triphosphate deoxynucleotide followed by a guanine triphosphate deoxynucleotide), and di- and tri-nucleotides. IAP can also convert adenosine triphosphate (ATP) to adenosine in the intestines, and this may have a protective effect in sepsis-induced acute kidney injury, because adenosine is a free radical scavenger and a vasodilator, which would help blood flow to improve oxygenation and prevent ischemia. Extracellular ATP (eATP) can be removed by conversion to adenosine by ectonucleotidases [e.g., cluster of differentiation 39 (CD39; ecto-apyrase) and cluster of differentiation 73 (CD73; ecto-5'-nucleotidase)] under homeostatic conditions; however, under pathological conditions involving inflammation and hypoxia, eATP levels in the bloodstream may increase due to active release from cells, passive leakage from damaged/dying cells, and down-regulation of ectonucleotidases. A proinflammatory and toxic role for eATP was reported to be due to activation of both P2X and P2Y purinogenic receptors, which could be prevented by dephosphorylation of ATP by apyrase, thereby preventing the production of inflammatory and destructive cytokines, including tumor necrosis factor (TNF) and interleukin-1 (IL-1), in a mouse model of LPS-induced inflammation. Removal of systemic eATP could be a useful strategy to reduce systemic inflammatory damage and toxicity in systemic inflammatory response syndrome (SIRS).

The dephosphorylation of ATP to adenosine diphosphate (ADP), and dephosphorylation of ADP to adenosine monophosphate (AMP) by AP, *Saccharomyces boulardii* AP (SBAP) and/or apyrase, followed by dephosphorylation of AMP to adenosine by CD73 on the endothelial cell surfaces of blood vessels enables in vivo conversion of ATP to adenosine, thereby reducing or inhibiting inflammation because adenosine is a free-radical scavenger and a vasodilator.

It is likely that use of APs including IAP, SBAP, apyrase/CD39 along with CD73, which is present on the endothelial cells lining blood vessels, may improve anti-inflammatory efficacy by insuring conversion of the eATP to adenosine and inorganic phosphate to restore homeostasis of tissues damaged by infection and inflammation. LPS may be recognized by Toll-like receptor-4/myeloid differentiation factor-2 (TLR4/MD2) complex, leading to the release of proinflammatory cytokines. Primary glucosamine linked side chains of LPS must be removed from lipid A before intestinal IAP can cleave either of the lipid A phosphate groups from some enteric LPS chemotypes. Acyloxyacyl hydrolase (AOAH) conversion of LPS to deacylated LPS (dLPS) may be the most likely mechanism for reducing the stimulatory potency of LPS in the intestines. This is in agreement with contemporary understanding of AOAH action, which is to remove the secondary acyl chains from lipid A to prevent lipid A recognition by TLR4/MD2 cellular receptors, thereby reducing inflammation caused by LPS.

The conversion of LPS to dLPS transforms LPS, a potent agonist of cellular inflammation, to an antagonist of inflammation, so AOAH conversion of LPS to dLPS enables in vivo conversion of proinflammatory LPS to dLPS, a competitive inhibitor of LPS for cellular attachment sites, thereby inhibiting inflammation caused by LPS.

Intestinal permeability increases as a result of ischemia during sepsis and septic shock. This allows digestive enzymes including trypsin, chymotrypsin and elastase to escape from the intestinal lumen and move into the wall of the intestine where these enzymes may activate matrix metalloproteinases (MMPs). This increases the overall proteolytic activity which facilitates translocation of LPS and these proteases into the bloodstream. Contemporary studies suggest significantly increased levels of trypsin-, chymotrypsin-, and elastase-like enzymes, and MMP-9 in plasma following hemorrhagic shock in rats. It is likely that the same scenario would hold during sepsis in humans and that such proteases in the bloodstream would cause fibrin formation and conversion of plasminogen into plasmin, which would exacerbate tissue damage and sepsis. Protease action would also digest enzymes and protein enzyme inhibitors immobilized in blood treatment devices. This could be prevented by use of antibodies against these proteases and by use of protease inhibitors.

In the human body, the fibrinolytic system functions to dissolve fibrin, one of the main products of thrombin activity. Two serine proteases: tissue plasminogen activator (tPA) and urokinase plasminogen activator (uPA) catalyze the conversion of plasminogen into the broad-spectrum protease plasmin, the major protease in this system. tPA and uPA may be inhibited by serine protease inhibitors (serpins) including plasminogen activator inhibitor-1 (PAI-1) and to a lesser extent, plasminogen activator inhibitor-2 (PAI-2). The fibrinolytic system may be down-regulated by use of antibodies against tPA, uPA, or plasmin and by protease inhibitors.

Complement is part of the innate immune system that protects humans against pathogens; however, it is often identified as an inducer of excessive inflammatory host responses that are believed to contribute to multiple organ failure and death in severe sepsis. The classical complement pathway may be activated by binding of antigen-antibody complexes to one of the C1 proteins, and this is followed by a cascade of reactions. Cleavage of complement C3 by a serine proteases including C3 convertase, thrombin, or plasmin leads to formation of C3a and C3b fragments. The anaphylatoxin C3a may activate platelets and cause their aggregation, increase vascular permeability, and promote extravasation of phagocytes. The C3b fragment may participate in opsonization, which involves phagocytosis of antibodies or bacteria, release of inflammatory peptides, and activation of the complement membrane attack complex to cause cell lysis. Protease inhibitors that bind C3 convertase and plasmin would abrogate this process, thereby reducing inflammation and formation of the membrane attack complex that could destabilize enzymes and protein enzyme inhibitors immobilized in the blood treatment devices described herein.

Neutrophils are important in host defense against infections and act as the first line of microorganism control. Neutrophil elastase (NE) is a serine protease that has antibacterial activity against Gram negative bacteria like *Escherichia coli*, it is active against a broad range of substrates, and it is an important factor promoting inflammation. Proteolytic enzymes in blood including elastase, plasmin, thrombin, and the membrane attack complex of complement may promote inflammation and destroy tissues in sepsis. These proteases may also destroy enzymes and enzyme inhibitors immobilized in blood treatment devices. This could be prevented by use of antibodies against these proteases and by use of protease inhibitors.

It is necessary to maintain activity and stability of enzymes and functional proteins immobilized on indwelling and extracorporeal bioreactors. Use of immobilized proteins that would not be recognized as "foreign" by the patient's immune system would be of paramount importance for preserving enzyme activity and maintaining stability of immobilized enzymes and enzyme inhibitors. This may require use of enzymes and antibodies against specific enzymes and enzyme inhibitors from human blood or tissues or prepared from the patient's blood or tissues by recombinant deoxyribonucleic acid (DNA) technology including antibodies against these proteases (e.g., anti-trypsin, anti-elastase, and anti-MMP-9), serine protein inhibitors (serpins) [e.g., alpha-1 antitrypsin inhibitor (A1AT), plasminogen activator inhibitor-1 (PA-1) and plasminogen activator inhibitor-2 (PA-2)], and $\alpha_2$-macroglobulin, which is able to inactivate a wide variety of proteases including plasmin, elastase, and MMPs.

Immobilization of one or more protease inhibitors or antibodies against these proteolytic enzymes in one or more in-dwelling blood treatment devices (e.g., stents, catheters, and stents and catheters with hollow-fiber constructs) and extracorporeal bioreactors with immobilized AP, SBAP, apyrase, CD39, CD73 and AOAH enzymes would reduce the levels of the circulating proteases in the bloodstream, thereby reducing the protease destruction of the immobilized enzymes and enzyme inhibitors in blood treatment devices that are the subject of this invention. Alternately, one or a plurality of the protease inhibitors may be co-immobilized in the same blood treatment device with one or a plurality of antibodies against proteolytic enzymes in in-dwelling blood treatment devices including stents, catheters, stents and catheters containing hollow-fiber bundles, and in extracorporeal blood treatment devices.

When LPS enters the bloodstream from the site of an infection or from the intestinal tract, it becomes bound to blood proteins including lipopolysaccharide binding protein (LBP). LBP is an acute phase protein produced primarily by hepatocytes, but it is also produced by non-hepatic tissues such as cells of the intestine, lungs, and gingiva. LBP forms high-affinity complexes with LPS by binding to the lipid A moiety of LPS. Immobilized LBP in indwelling or extracorporeal blood treatment devices would bind lipid A to sequester LPS and lower the concentration of LPS in the bloodstream of a patient to help prevent or treat sepsis and septic shock. A lowered concentration of LPS in the bloodstream may allow use of lower concentrations of enzymes in the bioreactor to prevent and/or treat sepsis.

Indwelling vascular devices include arterial and intravenous (IV) stents and catheters that are used to maintain patency, access blood, and administer IV fluids and medications to a patient. First generation stents, such as bare metal stents (BMS) made from 316L stainless steel, have been successful in maintaining blood flow in patients with atherosclerosis or blocked arteries. Drug eluting stents (DES) are made with a polymer that protects the medicine and releases it in a controlled manner over a period of time. Current studies suggest that polyurethane II vascular catheters are safe and provide long-indwelling vascular access for weeks, months or years in patients with cancer.

In-dwelling catheters for use in blood vessels generally are a thin, flexible tube, and stents are expandable metal or polymer devices that are inserted into a blood vessel, typically an artery, and expanded to maintain patency of that vessel. It is possible to enhance catheters and stents for immobilization by incorporating hollow fiber bundles into them to increase the interior surface area for the immobilized enzymes and other materials. The fiber bundles in such devices may be made from bio-compatible materials including polyamide (nylon), polysulfone, polyether sulfone, polyvinylidene fluoride (PVDF), and cellulose di- and tri-acetate. The fibers in the hollow-fiber bundles should have inner diameters of 50-500 µm to provide substantial surface area for immobilizing bioactive materials including enzymes and enzyme inhibitors and have sufficient diameter so to allow red blood cells, platelets, leukocytes, granulocytes, macrophages and neutrophils to pass through the hollow fibers without restricting blood flow.

The use of immobilized APs including SBAP and apyrase and AOAH enzymes in an extracorporeal blood treatment apparatus (e.g., a bioreactor) have been reported for detoxifying bacterial LPS and proinflammatory compounds in the bloodstream; however, other medical conditions including aging, cancer, diabetes, obesity, emotional stress and anxiety may cause increased intestinal permeability that results in translocation of LPS and proteases from the colon into the bloodstream to cause tissue damage and inflammation that may be treated by the blood treatment devices described herein. Although a patient may be treated with an extracorporeal bioreactor, there may be medical conditions for which it would be preferable to have continuous, long-term treatment, for example, over a period of weeks or months, so that it would be more suitable to have an indwelling bioreactor, such as a stent or a catheter, rather than to have an extracorporeal bioreactor for treating a patient's blood that may limit a patient's activities. The use of stents or catheters containing immobilized enzymes offers a way to provide long-term, hassle-free treatment of sepsis and inflammation due to microbial toxins and proinflammatory compounds; however, it would be necessary to use an extracorporeal bioreactor for treating a patient in situations where immediate treatment is needed or when a patient's physical condition will not allow surgery. Accordingly, there exists a need in the art for indwelling vascular devices and extracorporeal bioreactors with immobilized AP, IAP, SBAP, apyrase, CD39, CD73, and/or AOAH that may be used as a sole treatment for destroying LPS and other proinflammatory compounds in the bloodstream of a patient or as adjuncts to other treatments for sepsis and microbial infections.

In one embodiment, the alkaline phosphatase (AP) comprises *Saccharomyces boulardii* alkaline phosphatase (SBAP).

In one embodiment, the AP further comprises human intestinal alkaline phosphatase (IAP).

In one embodiment, the AP further comprises human cluster of differentiation 39 (CD39; ecto-apyrase).

In one embodiment, the AP further comprises human cluster of differentiation 73 (CD73; CD73; ecto-5'-nucleotidase).

In one embodiment, the AP further comprises apyrase.

In one embodiment, the acyloxyacyl hydrolase (AOAH) enzyme detoxifies LPS.

In one embodiment, the AP, IAP, SBAP, apyrase, CD39, CD73, and/or AOAH detoxify Gram negative bacterial lipopolysaccharide (LPS).

In one embodiment, the AP, IAP, SBAP, apyrase, CD39, CD73, and/or AOAH detoxify at least one of Gram negative LPS, Gram positive bacterial extracellular lipoteichoic acid, bacterial extracellular ATP, ADP, DNA, ribonucleic acid (RNA) and flagellin, yeast and fungal extracellular ATP, ADP, DNA and RNA, viral extracellular DNA and RNA, and host extracellular ATP, ADP, DNA, or RNA.

In one embodiment, AP, IAP, SBAP, apyrase, CD39, and CD73, dephosphorylate extracellular bacterial, yeast, and fungal nucleoside triphosphates including ATP, guanosine triphosphate (GTP), cytosine triphosphate (CTP), thiamine triphosphate (TTP), and uridine triphosphate (UTP) and extracellular bacterial, yeast, fungal and viral nucleotides including deoxyribonucleic acid (DNA) and ribonucleic acid (RNA).

In one embodiment, the APs detoxify biological agents contained within patient blood by dephosphorylation.

In one embodiment, the AOAH detoxifies biological agents contained within patient blood by deacylation.

In one embodiment, AP enzyme is immobilized by being covalently attached to the bioreactor surface.

In one embodiment, SBAP enzyme is immobilized by being covalently attached to the bioreactor surface.

In one embodiment, apyrase enzyme is immobilized by being covalently attached to the bioreactor surface.

In one embodiment, CD39 enzyme is immobilized by being covalently attached to the bioreactor surface.

In one embodiment, CD73 enzyme is immobilized by being covalently attached to the bioreactor surface.

In one embodiment, AOAH enzyme is immobilized by being covalently attached to the bioreactor surface.

In one embodiment, the bioreactor surface is the inner surface of a stent.

In one embodiment, the bioreactor surfaces are the one or more surfaces of a hollow fiber bundle within a stent.

In one embodiment, the bioreactor surface is the inner surface of a catheter.

In one embodiment, the bioreactor surfaces are the one or more surfaces of a hollow fiber bundle within a catheter.

In one embodiment, the hollow fiber bundle comprises 400 to 20,000 biocompatible hollow fibers made from synthetic materials including, but not limited to polysulfone, polyether sulfone, polymethylmethacrylate, ethylene vinyl alcohol copolymers, polyvinylidene fluoride (PVDF), and polyacrylonitrile, or made from natural materials including, but not limited to cellulose diacetate and cellulose triacetate, with an internal diameter of 50-500 µm, a wall thickness of 10 to 50 µm, and a length of 3 to 50 cm. The hollow fibers are arranged in parallel in the hollow fiber bundle.

In one embodiment, lipopolysaccharide binding protein (LBP) is immobilized by being covalently attached to the bioreactor surface.

In one embodiment, AP and apyrase enzymes each are immobilized by being covalently attached to separate bioreactor surfaces configured in series.

In one embodiment, AP and apyrase enzymes are co-immobilized by being covalently attached to a single bioreactor surface.

In one embodiment, SBAP and apyrase enzymes each are immobilized by being covalently attached to separate bioreactor surfaces configured in series.

In one embodiment, SBAP and apyrase enzymes are co-immobilized by being covalently attached to the same bioreactor surface.

In one embodiment, AP, apyrase, CD73 and AOAH enzymes each are immobilized by being covalently attached to separate bioreactor surfaces configured in series.

In one embodiment, AP, apyrase, CD73 and AOAH enzymes are co-immobilized by being covalently attached to the same bioreactor surface.

In one embodiment, apyrase, CD73 and AOAH enzymes and anti-trypsin each are immobilized by being covalently attached to separate bioreactor surfaces configured in series.

In one embodiment, apyrase, CD73 and AOAH enzymes and anti-trypsin are co-immobilized by being covalently attached to the same bioreactor surface.

In one embodiment, apyrase, CD73 and AOAH enzymes and anti-elastase each are immobilized by being covalently attached to separate bioreactor surfaces configured in series.

In one embodiment, apyrase, CD73 and AOAH enzymes and anti-elastase are co-immobilized by being covalently attached to the same bioreactor surface.

In one embodiment, SBAP, CD39, CD73 and AOAH enzymes each are immobilized by being covalently attached to separate bioreactor surfaces configured in series.

In one embodiment, SBAP, CD39, CD73 and AOAH enzymes are co-immobilized by being covalently attached to the same bioreactor surface.

In one embodiment, IAP, apyrase, CD73 and AOAH enzymes each are immobilized by being covalently attached to separate bioreactor surfaces configured in series.

In one embodiment, IAP, apyrase, CD73 and AOAH enzymes are co-immobilized by being covalently attached to the same bioreactor surface.

In one embodiment, SBAP, CD39, CD73 and AOAH enzymes and $\alpha_2$-macroglobulin each are immobilized by being covalently attached to separate bioreactor surfaces configured in series.

In one embodiment, SBAP, CD39, CD73 and AOAH enzymes and $\alpha_2$-macroglobulin are co-immobilized by being covalently attached to the same bioreactor surface.

In one embodiment, IAP, apyrase and AOAH enzymes and alpha-1 antitrypsin inhibitor (A1AT) each are immobilized by being covalently attached to separate bioreactor surfaces configured in series.

In one embodiment, IAP, apyrase and AOAH enzymes and A1AT are co-immobilized by being covalently attached to the same bioreactor surface.

In one embodiment, SBAP, CD39, CD73 and AOAH enzymes and A1AT each are immobilized by being covalently attached to separate bioreactor surfaces configured in series.

In one embodiment, SBAP, CD39, CD73 and AOAH enzymes and A1AT are co-immobilized by being covalently attached to the same bioreactor surface.

In one embodiment, IAP, apyrase and AOAH enzymes, A1AT, and lipopolysaccharide binding protein (LBP) each are immobilized by being covalently attached to separate bioreactor surfaces configured in series.

In one embodiment, IAP, apyrase and AOAH enzymes, A1AT, and LBP are co-immobilized by being covalently attached to the same bioreactor surface.

In one embodiment, SBAP, CD39, CD73 and AOAH enzymes, A1AT, and LBP each are immobilized by being covalently attached to separate bioreactor surfaces configured in series.

In one embodiment, SBAP, CD39, CD73 and AOAH enzymes, A1AT, and LBP are co-immobilized by being covalently attached to the same bioreactor surface.

In one embodiment, IAP, apyrase and AOAH enzymes and plasminogen activator inhibitor-1 (PAI-1) each are immobilized by being covalently attached to separate bioreactor surfaces configured in series.

In one embodiment, IAP, apyrase and AOAH enzymes and PAI-1 are co-immobilized by being covalently attached to the same bioreactor surface.

In one embodiment, SBAP, CD39, CD73 and AOAH enzymes and PAI-1 each are immobilized by being covalently attached to separate bioreactor surfaces configured in series.

In one embodiment, SBAP, CD39, CD73 and AOAH enzymes and PAI-1 are co-immobilized by being covalently attached to the same bioreactor surface.

In one embodiment, the bioreactor surface further comprises one or more surfaces of a hollow fiber bundle within a catheter.

In one embodiment, the bioreactor surface further comprises one or more surfaces of a plurality of hollow fiber bundles within a catheter.

In one embodiment, the bioreactor surface further comprises one or more surfaces of a hollow fiber bundle within an extracorporeal bioreactor.

In one embodiment, the bioreactor surface further comprises one or more surfaces of one or a plurality of hollow fiber bundles within an extracorporeal bioreactor.

In one embodiment, the hollow fiber bundle for stents comprises 400 to 1,000 polysulfone fibers with an internal diameter of 50-500 µm and a length of 3-10 cm enclosed within the stent.

In one embodiment, the hollow fiber bundle for catheters comprises 400 to 1,000 polysulfone fibers with an internal diameter of 50-500 µm and a length of 3-10 cm enclosed in bio-compatible tubing including, but not limited to Tygon® (silicone) and polyurethane II tubing.

In one embodiment, the hollow fiber bundle for extracorporeal bioreactors comprises 400 to 20,000 polysulfone fibers with an internal diameter of 50-500 µm and a length of 3-25 cm enclosed in Tygon® (silicone) or polyurethane II tubing.

In one embodiment, the bioreactor is comprised of a nickel-titanium alloy stent.

In one embodiment, the bioreactor is comprised of a hollow fiber bundle within a nickel-titanium alloy stent.

In one embodiment, the bioreactor is comprised of a polyurethane II catheter.

In one embodiment, the bioreactor is comprised of a hollow fiber bundle within a polyurethane II catheter.

In one embodiment, the bioreactor is comprised of a polysulfone hollow fiber bundle within a polyurethane II catheter.

In one embodiment, the bioreactor is comprised of a 316L stainless steel stent.

In one embodiment, the bioreactor is comprised of a hollow fiber bundle within a 316L stainless steel stent.

In one embodiment, the bioreactor is comprised of a polysulfone hollow fiber bundle within a 316L stainless steel stent.

In one embodiment, the bioreactor is comprised of a cellulose triacetate hollow fiber bundle within a 316L stainless steel stent.

In one embodiment, the bioreactor is comprised of a hollow fiber bundle within an extracorporeal blood treatment device.

In one embodiment, the bioreactor is comprised of a polysulfone hollow fiber bundle within an extracorporeal blood treatment device.

In one embodiment, the bioreactor is comprised of a polyether sulfone hollow fiber bundle within an extracorporeal blood treatment device.

In one embodiment, the bioreactor is comprised of a polyvinylidene fluoride (PVDF) hollow fiber bundle within an extracorporeal blood treatment device.

In one embodiment, the bioreactor is comprised of a cellulose triacetate hollow fiber bundle within an extracorporeal blood treatment device.

In one embodiment, the bioreactor is comprised of a cellulose diacetate hollow fiber bundle within an extracorporeal blood treatment device.

In one embodiment, a patient's heartbeats urge blood through a stent inlet and outlet in fluid connection to the circulatory system of the patient.

In one embodiment, a patient's heartbeats urge blood through a stent with a fiber bundle inlet and outlet in fluid connection to the circulatory system of the patient.

In one embodiment, a patient's heartbeats urge blood through a catheter inlet and outlet in fluid connection to the circulatory system of the patient.

In one embodiment, a patient's heartbeats urge blood through a catheter with a fiber bundle inlet and outlet in fluid connection to the circulatory system of the patient.

In one embodiment, a patient's heartbeats urge blood through an extracorporeal blood treatment device with a hollow fiber bundle inlet and outlet in fluid connection to the circulatory system of the patient.

In one embodiment, blood of the patient is treated in an extracorporeal blood treatment device by connecting a blood transfer line to a vein in the patient's left forearm and pumping the patient's blood to a bioreactor with a peristaltic pump. The blood is treated in the bioreactor and then it is pumped back to a vein in the patient's left forearm via a blood transfer line.

In one embodiment, the bioreactor surface is provided with a continuous blood flow from the patient that continues until the biological agent(s) being detoxified have been reduced to predetermined levels.

In one embodiment, a blood detoxification system comprises an indwelling medical device having an inlet and outlet able to be placed in in fluid connection to the circulatory system of a patient. This indwelling medical device is a bioreactor, which consists of a stent containing a hollow fiber bundle with attached AP, SBAP, apyrase, and/or AOAH enzymes that can irreversibly detoxify biological agents contained within patient blood.

In one embodiment, phosphatase enzymes including any of known human AP isozymes including intestinal AP (TAP), tissue-nonspecific AP (TNAP), placental AP (PLAP), and germ cell AP (GCAP), any of other human phosphatase including apyrase/cluster of differentiation 39 (CD39; ecto-apyrase), cluster of differentiation CD73 (CD73; ecto-5'-nucleotidase), any of synthetic or man-made AP, such as AP made from recombinant DNA including *Escherichia coli*, any of human or animal apyrase/CD39 or AP and human nucleotidases including human CD73/ecto-5'-nucleotidase, bovine intestinal alkaline phosphatase, calf intestinal alkaline phosphatase, potato apyrase, and AP from shrimp and recombinant DNA technology (*E. coli* alkaline phosphatase) can be used, and addition of AOAH to the phosphatase enzymes may help insure destruction of all forms of circulating LPS in the bloodstream.

In one embodiment, detoxifying biological agents using AP, IAP, SBAP, apyrase, CD39, CD73, and/or AOAH are used to prevent or therapeutically treat at least one of sepsis, septic shock, inflammation, bacteremia, yeast infections, fungal infections, viral infections, systemic inflammatory response syndrome (SIRS), Gram negative bacterial lipopolysaccharide (LPS) in patient blood, Gram positive bacterial lipoteichoic acid in patient blood, inflammatory bowel disease (IBD), inflammatory bowel syndrome (IBS), Crohn's disease, ulcerative colitis, enterocolitis, necrotizing enterocolitis (NEC), meningitis, meningococcemia, trauma or hemorrhagic shock, burns, liver disease, pancreatitis, periodontal disease, pneumonia, cystic fibrosis, asthma, alpha-1 antitrypsin (A1AT) deficiency, chronic obstructive pulmonary disease (COPD), pulmonary fibrosis, tuberculosis, coronary heart disease, congestive heart failure, infectious endocarditis, renal disease, hemolytic uremic syndrome, kidney disease, autoimmune diseases including rheumatoid arthritis, systemic lupus erythematosus, mast cell activation disorders, cancer, diabetes, infection resulting in LPS or lipoteichoic acid in patient blood, abscesses resulting in LPS or lipoteichoic acid in patient blood, protein aggregation disorders including neurodegenerative diseases, Alzheimer's disease, Parkinson's disease, Huntington's chorea, macular degeneration, amyloidosis, and amyotrophic lateral sclerosis, arthritis, atherosclerosis, and patients undergoing surgery and transplants.

BRIEF SUMMARY OF THE INVENTION

This disclosure describes a system, apparatus and method that can accomplish therapeutic destruction of selected toxins, including but not limited to LPS and proinflammatory compounds within a biological system that are caused by medical conditions including microbial infections, sepsis and septic shock, by continuous passage of the blood of a patient through indwelling and extracorporeal bioreactors containing immobilized APs and AOAH enzymes, LBP and protease inhibitors. Treatment of a patient's blood converts LPS and extracellular ATP in blood into inhibitors of inflammation in vivo without adding any chemicals to the bloodstream of the patient.

BRIEF DESCRIPTION OF THE DRAWINGS

Embodiments will be readily understood by the following detailed description in conjunction with the accompanying drawings.

DETAILED DESCRIPTION OF THE INVENTION

This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, the term "about", when used in reference to numerical ranges, cutoffs, or specific values, is used to indicate that the recited values may vary by up to as much as 10% from the listed value. As many of the numerical values used herein are experimentally determined, it should be understood by those skilled in the art that such determinations can, and often times, will vary among different experiments. The values used herein should not be considered unduly limiting by virtue of this inherent variation. The term "about" is used to encompass variations of this sort up to, or equaling, 10%.

The term "attach," "attached" or "attachment" as used herein, refers to connecting or uniting by a chemical bond, link, or force in order to keep two or more chemical compounds, polymers, proteins, polysaccharides, lipids, nucleic acids, or other biological or manufactured compositions together.

As used herein, "for example," "for instance," "such as," or "including" are meant to introduce examples that further clarify a more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

Disclosed herein is an indwelling medical device, system or methods involving circulating, perfusing, or otherwise passing blood or other patient fluids through a system and device connected to or implanted into the circulatory system of a patient. One or more internal surfaces of the extracorporeal or indwelling medical device include immobilized enzymatic agents to interact with one or more patient fluid borne biologic agents. The medical device, system or methods provide a platform that can be applied to numerous conditions and diseases involving circulating cells, compounds, or other biologic agents, such as those associated with bacterial, yeast, fungal, or viral infection, cell death, sepsis, cancer, and many others.

Figure 1:
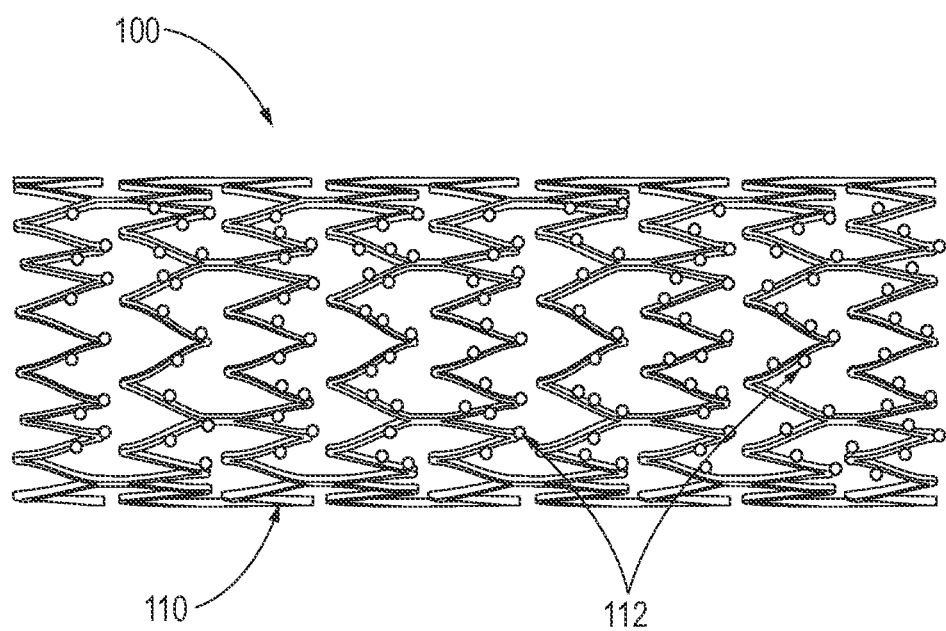
FIG. 1 illustrates one embodiment of a metal stent which can be inserted into the circulatory system of a patient to receive and treat blood or other fluids in a patient.

FIG. 1 illustrates one embodiment of a blood treatment device 100 comprised of a metal stent 110 with immobilized alkaline phosphatase (AP) enzymes 112, which can be inserted into the circulatory system of a patient to receive and treat blood or other fluids in a patient. AP enzymes 112 have a wide range of substrates and APs are able to dephosphorylate Gram negative bacterial lipopolysaccharide (LPS), nucleoside triphosphates including adenosine triphosphate (ATP), nucleotide diphosphates including adenosine diphosphate (ADP), and nucleotides including deoxyribonucleic acid (DNA) and ribonucleic acid (RNA).

Figure 2A:
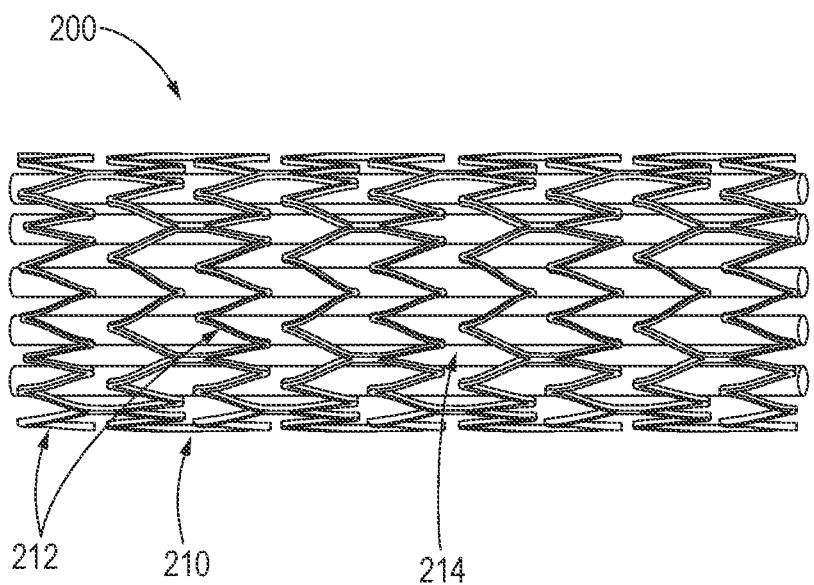
FIG. 2A illustrates a stent placed horizontally.
Figure 2B:
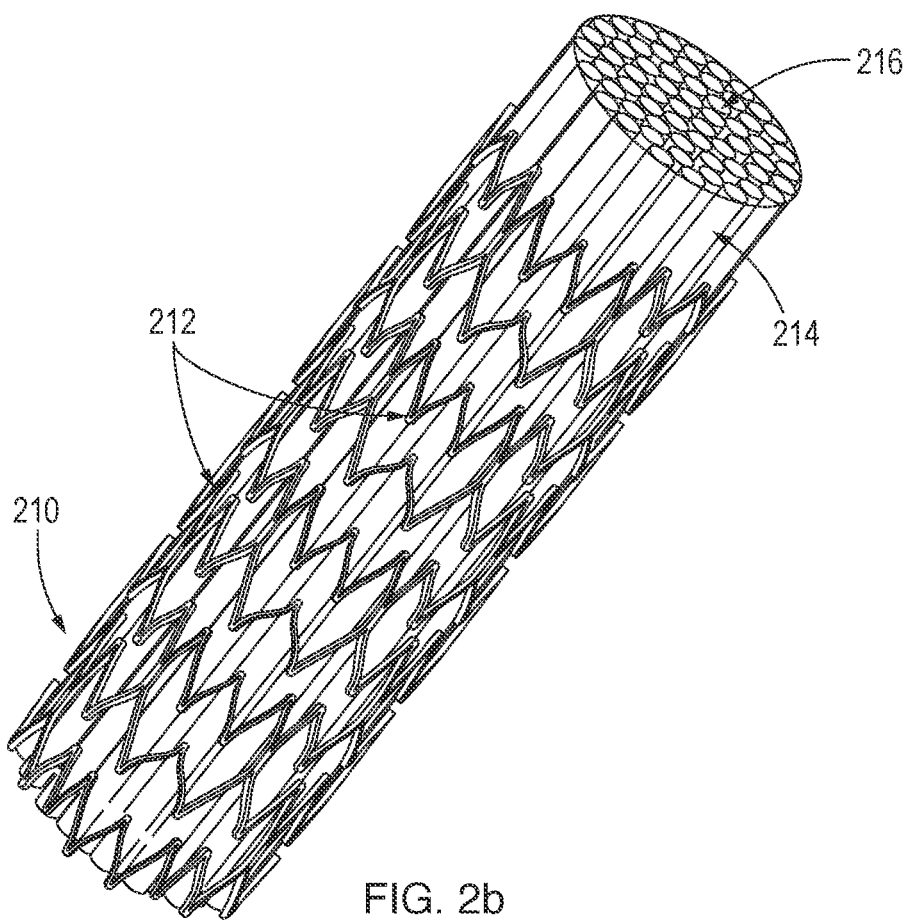
FIG. 2B illustrates a stent positioned at a 45-degree angle from horizontal.

FIG. 2 illustrates one embodiment of a blood treatment device 200 comprising a stent 210 with stainless steel metal components 212. FIG. 2a shows the stent 210 placed horizontally, and the hollow fiber bundle 214 is surrounded by the stainless steel metal components 212 of the stent 210. FIG. 2b shows the stent 210 positioned at a 45-degree angle from horizontal. The hollow fiber bundle 214 is surrounded by the metal components 212 of the stent 210, and the circular openings 216 of many tubes in the hollow fiber bundle 214 are shown.

Figure 3:
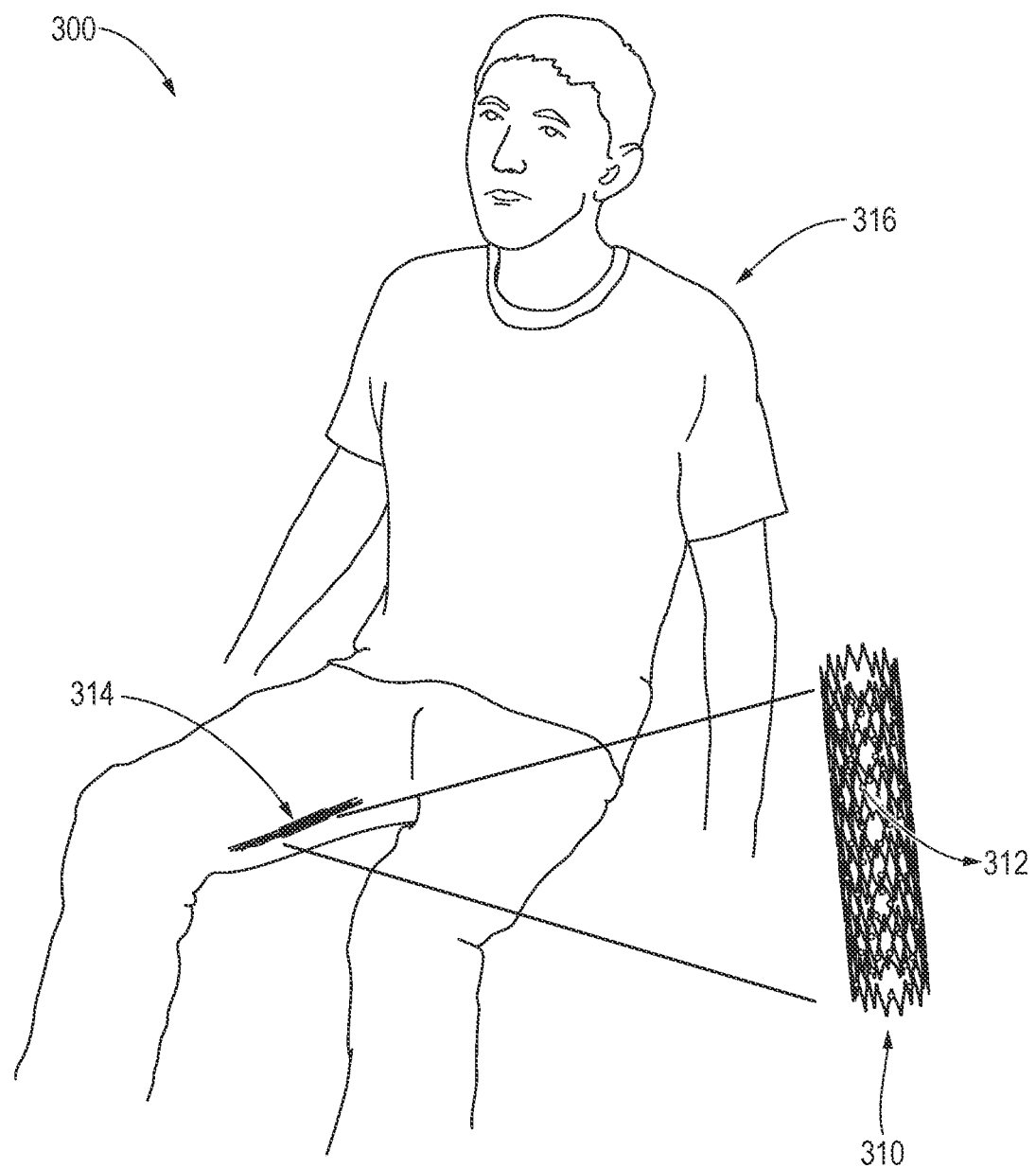
FIG. 3 illustrates one embodiment of an indwelling stent containing a hollow fiber bundle with immobilized enzymes, implanted into the right femoral artery of a patient to receive and treat blood.

FIG. 3 illustrates one embodiment of a blood treatment device 300 comprised of an indwelling stent 310 with immobilized enzymes 312, implanted into the right femoral artery 314 of a patient 316 to treat the patient's blood.

AP from bovine kidney (Calzyme, 200 units/mg) was covalently immobilized to carboxylate modified non-porous 20 nm polystyrene (PS—COOH) beads (e.g., Bang Laboratories, Cat. #PC07003) by dispersing 1.2 mg of AP in 0.5 ml PolyLink Coupling Buffer (e.g., Polysciences, Cat. #24350), followed by passing the enzyme through a 5 ml SpinOUT™ GT-600 column (e.g., G-Biosciences, Cat. #786-704) preequilibrated PolyLink Coupling Buffer to ensure removal of any amine component in the reconstituted AP. For the coupling reaction, 50 µl of PS—COOH beads were washed with PolyLink Coupling Buffer, centrifuged, and resuspended in 0.17 ml of PolyLink Coupling Buffer. Then 0.5 ml of SpinOUT™ GT-600 column passed AP was added to these beads followed by 50 µl of 200 mg/ml 1-ethyl-3-(3-dimethylamino-propyl) carbodiimide hydrochloride (EDAC) solution in PolyLink Coupling buffer, followed by incubation at room temperature for 2 hours, washing, and centrifugation to remove the PolyLink Coupling buffer to yield the PS beads with immobilized AP (AP PS beads). The AP PS beads were then stored in storage buffer [2 M $(NH_4)_2SO_4$, 1 mM $MgCl_2$, 0.4 mM $ZnCl_2$] at 4° C.

Dephosphorylation of LPS and ATP was demonstrated with a simulated stent comprised of a 100 µl column containing 50 µl PS beads with immobilized AP (AP PS beads). As a control, 50 µl of PS—COOH beads without immobilized AP was added to another 100 µl column. The columns each were equilibrated with 5 ml of 10 mM (N,N-bis(2-hydroxyethyl)-2-aminoethanesulfonic acid (BES), 1 mM $MgCl_2$, 0.1 mM $ZnCl_2$ buffer (BES buffer) at pH 7.4, with a flow rate of 0.4 ml/min for equilibration. The experiments used a flow rate of 0.2 ml/min.

Figure 4:
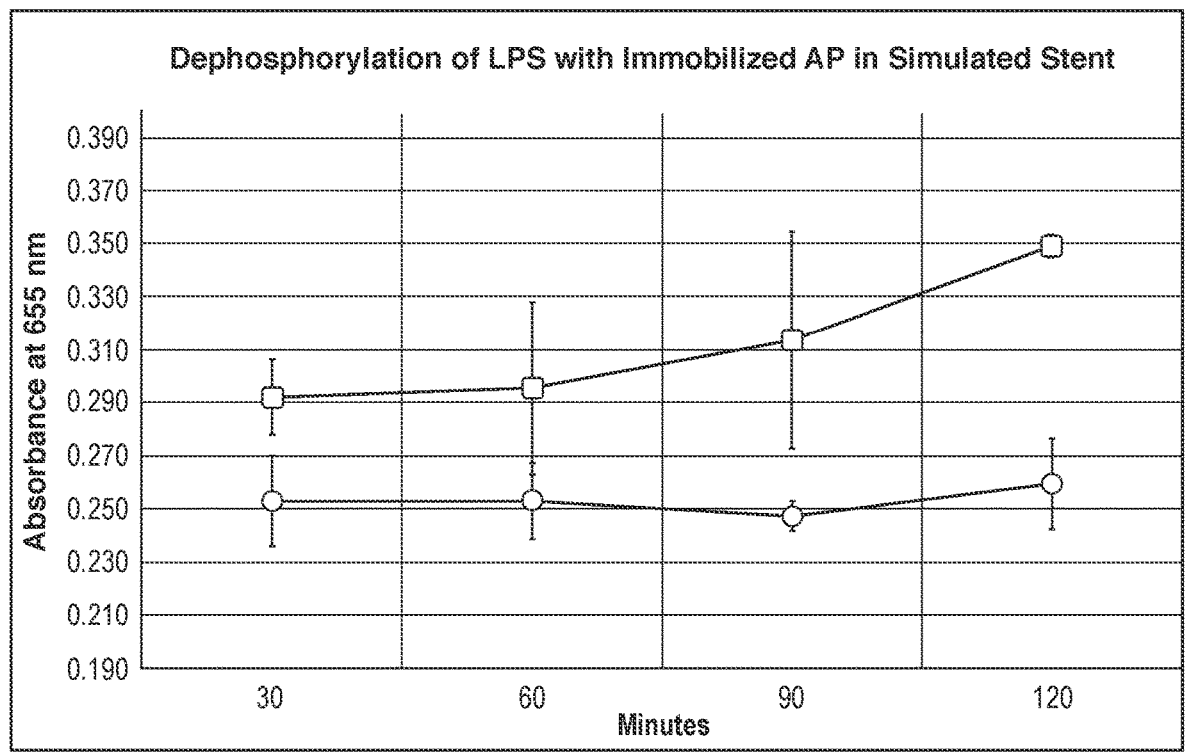
FIG. 4 illustrates destruction of LPS by immobilized AP in an aqueous buffer following passage through a simulated stent, a blood treatment apparatus comprised of a column with AP immobilized on polystyrene microbeads (AP PS beads), using the Malachite Green Assay with absorbance at 655 nm ($A_{655}$) to measure phosphate ions released into the buffer as a result of AP dephosphorylation of LPS at different time points as the buffer with LPS was recirculated from the reservoir, to the column, and back to the reservoir.

FIG. 4 illustrates the irreversible destruction of LPS by immobilized AP in an aqueous buffer at pH 7.4 following passage through a simulated stent, comprised of a column with AP PS beads, using the Malachite Green Assay with absorbance at 655 nm ($A_{655}$) to measure phosphate ions released into the buffer as a result of AP dephosphorylation of LPS at different time points as the buffer with LPS was recirculated from the reservoir to the column, and back to the reservoir.

Malachite green binds to the inorganic phosphate released as AP dephosphorylates LPS to give a dark green color that is measured at $A_{655}$. No initial $A_{655}$ measurements are shown in FIG. 4 because the volume of BES buffer in the tubing used to pump LPS in BES buffer from the reservoir to the column and back to the reservoir diluted the LPS concentration in the BES buffer. Malachite green also binds to LPS and causes absorbance at $A_{655}$. However, the free inorganic phosphate increased significantly (p<0.01) at one hour in the BES buffer when LPS was passed through the column with immobilized AP PS beads during the 120 minute experiment, demonstrating dephosphorylation of LPS (upper curve with square data points); whereas the BES buffer with LPS passed through the column with PS beads without immobilized AP (i.e., the control, the lower curve with round data points) showed no significant increase in $A_{655}$ and therefore no significant dephosphorylation of LPS during the 120 minute experiment, which was performed with duplicate readings at each time point.

Dephosphorylation of ATP was demonstrated by the luminescence assay, as follows: One vial of ATP detection buffer was added to one vial of ATP detection substrate (e.g., by G-Biosciences, Cat. #786-1311) and mixed to get the ATP assay solution. The 2 µM ATP solution was circulated from the reservoir, through the column packed with immobilized AP PS beads, and back to the reservoir, and 100 µl test samples were taken from the reservoir every 30 minutes up to 120 minutes. For the control, the ATP solution was passed through the column with PS—COOH beads without immobilized AP, and the samples were added to separate wells on a 96-well opaque white microtiter plate. Then, 100 µl of ATP assay solution was added to each well containing samples and controls. The microtiter plate was incubated in the dark for 10 minutes before taking luminescence readings of each well, with the luminometer set to perform a 1.6 second measurement delay followed by the 10 second measurement per sample per well.

Figure 5:
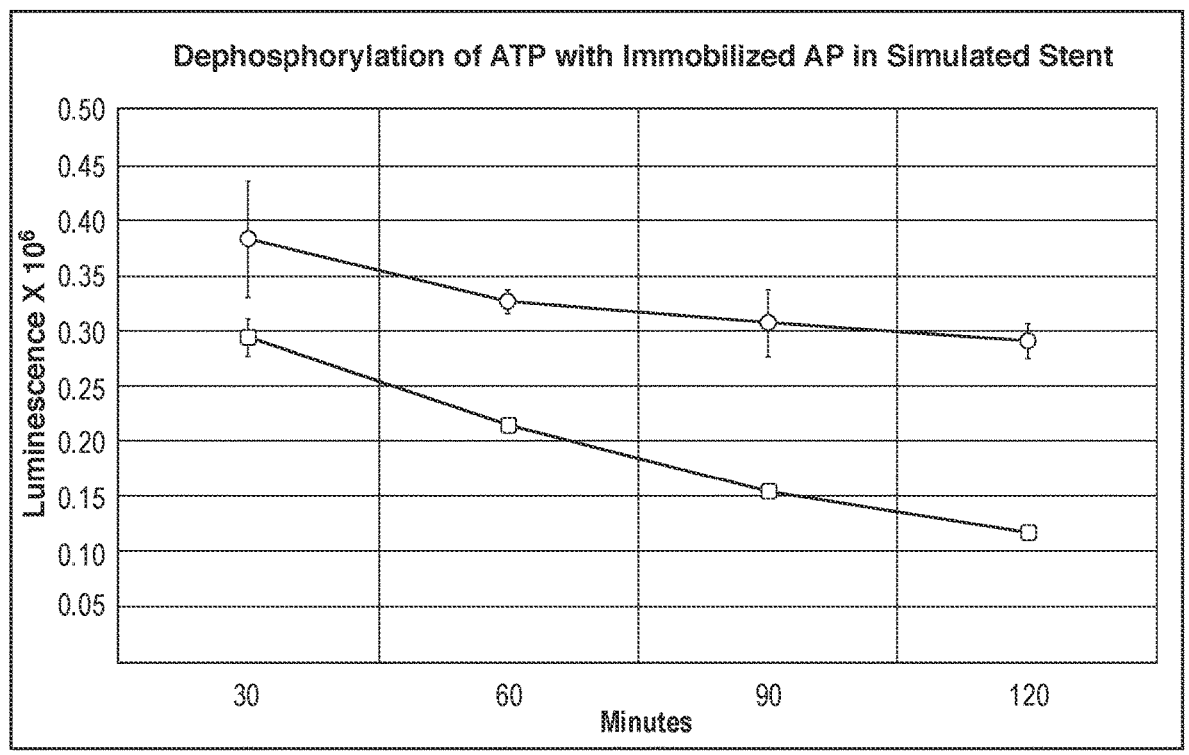
FIG. 5 illustrates destruction of ATP by immobilized AP in an aqueous buffer following passage through a simulated stent, a blood treatment apparatus comprised of a column with AP PS beads, using luminescence to determine ATP remaining in the buffer at different time points as the buffer with ATP was recirculated from the reservoir to the column, and back to the reservoir.

FIG. 5 illustrates the irreversible dephosphorylation of ATP in BES buffer at pH 7.4 due to passage through a simulated stent comprised of a column with immobilized AP PS beads. ATP dephosphorylation was measured with the Lumino™ Detection Assay (e.g., by G-Biosciences, St. Louis, MO) in which ATP concentrations were determined by bioluminescence based on ATP levels remaining in the buffer at different time points as the buffer with ATP was recirculated from the reservoir to the column, and back to the reservoir. FIG. 5 shows there was a significant (p<0.001) decrease in ATP concentration in the ATP solution passed through the simulated stent containing immobilized AP PS beads during the 120 minute experiment (lower line with square data points that are larger than the vertical error bars at 60, 90 and 120 minutes), which demonstrates dephosphorylation of ATP. Although the ATP solution that was passed through the column with PS—COOH beads without immobilized AP (control, upper curve with round data points) showed a slight decrease in luminescence during the 120 minute experiment, it was significantly different (p<0.001) from the experimental data luminescence during the experiment which was performed with duplicate readings at each time point.

EXAMPLE 1

In one example embodiment, a bioreactor comprised of a Boston Scientific Innova® self-expanding Nitinol (nickel-titanium) alloy stent, catalog No. 39293-06157, with a length of 150 mm and width of 6 mm, with 2,000 U human intestinal AP (IAP) immobilized on the surfaces of this stent is prepared using the procedures described in [00119], with the exception of replacing the polystyrene beads used in [00119] with this stent. After immobilization is completed, the stent is placed in a paper or plastic container, which is sealed and sterilized by a dose of 25 kGy ionizing radiation so that it may be used immediately or stored in a refrigerator at 4° C. for several months prior to use. The stent is aseptically removed from the container at the time of surgical implantation.

This sterile Nitinol stent with 2,000 U human IAP immobilized on the surfaces may be surgically implanted into the right femoral artery of a patient to help prevent sepsis after identification of a serious E. coli infection. IAP in this stent will destroy LPS, flagellin and extracellular proinflammatory compounds including extracellular ATP (eATP), extracellular ADP (eADP), extracellular DNA (eDNA), and extracellular RNA (eRNA), released into the bloodstream due to this infection because the immobilized IAP in the bioreactor irreversibly dephosphorylates approximately 10% of the LPS, flagellin eATP, eADP, eDNA, and eRNA in the blood of the patient each hour as the blood passes through this bioreactor. In addition, the dephosphorylation of eADP results in the formation of extracellular adenosine monophosphate (eAMP) and phosphate, and this eAMP may be dephosphorylated by cluster of differentiation 73 (CD73) on endothelial cells and tissues to yield adenosine plus phosphate. Adenosine is a vasodilator and an anti-inflammatory compound, so that the proinflammatory eATP in blood is transformed into an inhibitor of inflammation in vivo without adding any chemicals to the bloodstream of the patient, thereby ameliorating inflammation caused by the infection and reducing the likelihood of sepsis in this patient. The stability (i.e., half-life) of enzymes generally is increased by immobilization, which enables the bioreactor to retain a substantial percentage of the original IAP activity while implanted in the patient for up to 6 weeks.

EXAMPLE 2

In one example embodiment, a bioreactor comprises a titanium oxynitride-coated stainless steel stent, 80 mm long and 5 mm wide, with 1,000 U human apyrase immobilized on the surfaces of this stent. After immobilization is completed, the stent is placed in a paper or plastic container, which is sealed and sterilized by a dose of 25 kGy ionizing radiation so that it may be used immediately or stored in a refrigerator at 4° C. for several months prior to use. The stent is aseptically removed from the container at the time of surgical implantation.

This sterile titanium oxynitride-coated stainless steel stent with 1,000 U human apyrase immobilized on the surfaces may be surgically implanted into the left subclavian artery of a patient with COVID-19 infection after admission into a hospital intensive care unit (ICU) for prophylactic treatment to destroy proinflammatory compounds including eATP, eADP, eDNA, and eRNA released into the bloodstream from the severe acute respiratory syndrome coronavirus 2 (SARS-CoV-2) and damaged host tissues. The apyrase in the bioreactor irreversibly dephosphorylates approximately 10% of the extracellular nucleotides and nucleoside triphosphates in the blood of a patient each hour in vivo as the blood passes through this bioreactor, including formation of AMP from eATP, which is further converted to adenosine and phosphate by CD73 on endothelial cells in blood vessels, thereby abrogating sepsis. This bioreactor may retain greater than 50% of the original apyrase activity while implanted in the patient for at least one month.

EXAMPLE 3

In one example embodiment, treatment of a patient is accomplished with two bioreactors in series. 1,000 U *Saccharomyces boulardii* AP (SBAP) are immobilized on the surfaces of the first polystyrene stent, which is 32 mm long and 6 mm wide, and 2,000 U acyloxyacyl hydrolase (AOAH) are immobilized on the second polystyrene stent, which is 32 mm long and 6 mm wide. After the immobilization procedures are completed, the stents are placed in separate paper or plastic containers, which are sealed and sterilized by a dose of 25 kGy ionizing radiation so that these stents may be used immediately or stored in a refrigerator at 4° C. for several months prior to use. The stents are aseptically removed from the containers at the time of surgical implantation.

The first sterile polystyrene stent with 1,000 U SBAP and the second sterile polystyrene stent with 2,000 U of AOAH immobilized on the lumen surfaces may be surgically implanted in series into the left femoral artery of a patient shortly after determination that this patient has sepsis to irreversibly dephosphorylate LPS, flagellin, proinflammatory nucleotides and triphosphate nucleosides in the bloodstream of the patient to enable in vivo conversion of eATP to adenosine and irreversible deacylation of LPS to deacylated LPS (dLPS). These stents retain a substantial percentage of the original SBAP and AOAH activities for about 2 months.

EXAMPLE 4

In one example embodiment, treatment of a patient is accomplished with two bioreactors in series. 1,000 U SBAP and 2,000 U AOAH are co-immobilized on the surfaces of the first polystyrene stent, 32 mm long and 4 mm wide, and 100 µg of polyclonal human anti-trypsin antibody are immobilize on the second polystyrene stent, 32 mm long and 4 mm wide. After the immobilization procedures are completed, the stents are placed in separate paper or plastic containers, which are sealed and sterilized by a dose of 25 kGy ionizing radiation so that these stents may be used immediately or stored in a refrigerator at 4° C. for several months prior to use. The stents are aseptically removed from the containers at the time of surgical implantation.

The sterile polystyrene stents with 1,000 U SBAP and 2,000 U of AOAH immobilized on the lumen surfaces of the first stent and 100 µg of anti-trypsin immobilized on the lumen surfaces of the second stent may be surgically implanted in series into the left femoral artery of a patient shortly after determination that this patient has sepsis to irreversibly dephosphorylate LPS, flagellin, and proinflammatory nucleoside triphosphates including eATP in the bloodstream of the patient to enable in vivo conversion of eATP to adenosine, irreversible deacylation of LPS to deacylated LPS (dLPS), and anti-trypsin protection from trypsin that may have translocated from the gastrointestinal tract into the bloodstream of the patient. Anti-trypsin binding of trypsin in the bloodstream would help preserve the enzymatic activity of immobilized enzymes in the bioreactor; however, anti-trypsin binding of trypsin would decrease over time as the antibody binding sites become saturated with bound trypsin. These bioreactors retain a substantial percentage of the original SBAP and AOAH activities while implanted in the patient for at least 2 months.

EXAMPLE 5

In one example embodiment, treatment of a patient is accomplished with two stents in series. These stents contain enzymes in the first stent and protease inhibitors in the second stent. 1,000 U human recombinant intestinal alkaline phosphatase (hrIAP), 500 U human CD73, and 2,000 U AOAH are co-immobilized on a hollow fiber bundle, 32 mm long and 10 mm wide, in the first polystyrene stent, and 100 µg of alpha-1 antitrypsin inhibitor (A1AT) are immobilized on the hollow fiber bundle in the second polystyrene stent, 32 mm long and 6 mm wide. After the immobilization procedures are completed, the stents are placed in separate paper or plastic containers, which are sealed and sterilized by a dose of 25 kGy ionizing radiation so that these stents may be used immediately or stored in a refrigerator at 4° C. for several months prior to use. The stents are aseptically removed from the containers at the time of surgical implantation.

The sterile polystyrene stents with 1,000 U hrIAP, 500 U human CD73, and 2,000 U of AOAH immobilized on the interior surfaces of the hollow fiber bundle of the first stent and 100 µg of A1AT immobilized on the lumen surfaces of the hollow fiber bundle of the second stent may be surgically implanted in series into the right femoral artery of a patient shortly after determination that this patient has sepsis. A1AT binding of serine proteases would help preserve the enzymatic activity of immobilized enzymes, although binding to proteases would decrease the efficacy of A1AT binding to other proteases over time. These bioreactors retain a substantial percentage of the original hrIAP, CD73 and AOAH activities while implanted in the patient for at least 2 months.

EXAMPLE 6

In one example embodiment, treatment of a patient is accomplished with an extracorporeal bioreactor comprised of a polysulfone hollow fiber bundle 32 mm long and 20 mm wide within polyurethane II tubing 21 mm wide and 40 mm long, in which 1,000 U hrIAP, 500 U human CD73, 2,000 U AOAH, and 1 mg of A1AT are co-immobilized on the surfaces of the polysulfone hollow-fiber bundle. After the immobilization procedures are completed, the tubing with the hollow fiber bundle is placed in a paper or plastic container, which is sealed and sterilized by a dose of 25 kGy ionizing radiation so that the blood treatment device may be used immediately or stored in a refrigerator at 4° C. for several months prior to use. The blood treatment device is aseptically removed from the container at the time it is connected to the patient.

The sterile bioreactor with 1,000 U hrIAP, 500 U human CD73, 2,000 U of AOAH and 1 mg of A1AT co-immobilized on the interior surfaces of the hollow fiber bundle of the extracorporeal bioreactor may be connected to a vein in the left arm of a patient shortly after determination that this patient has sepsis. A1AT binding of serine proteases would help preserve the enzymatic activity of immobilized enzymes, although binding to proteases would decrease the efficacy of A1AT sequestering other proteases over time. These bioreactors retain a substantial percentage of the original hrIAP, CD73, and AOAH activities for at least 2 months.

EXAMPLE 7

In one example embodiment, treatment of a patient is accomplished with an extracorporeal bioreactor containing two polyether sulfone hollow fiber bundles, in series, enclosed in polyurethane II tubing 70 mm long. 2,000 U human recombinant intestinal alkaline phosphatase (hrIAP), 1,000 U human CD73, and 4,000 U AOAH are co-immobilized on the first polyether sulfone hollow fiber bundle, which is 32 mm long and 20 mm wide, and 50 µg A1AT and 1 mg $\alpha_2$-macroglobulin are co-immobilized on the second polyether sulfone hollow-fiber bundle, which is 32 mm long and 20 mm wide, and situated in series with the first hollow fiber bundle within the polyurethane II tubing that is 21 mm wide and 70 mm long. After the immobilization procedures are completed, the bioreactor is placed in a paper or plastic container, which is sealed and sterilized by a dose of 25 kGy ionizing radiation so that this blood treatment device may be used immediately or stored in a refrigerator at 4° C. for several months prior to use. The blood treatment device is aseptically removed from the container at the time it is connected to the patient.

The sterile bioreactor with 2,000 U hrIAP, 1,000 U human CD73, and 4,000 U of AOAH immobilized on the interior surfaces of the first hollow fiber bundle and connected in series with 50 µg A1AT and 1 mg of $\alpha_2$-macroglobulin immobilized on the interior surfaces of the second hollow fiber bundle is connected to a vein in the patient's left forearm, with blood transfer lines leading from the patient to a peristaltic pump, to the bioreactor, and back to a vein in the patient's left forearm shortly after determination that this patient has sepsis. Although the A1AT and $\alpha_2$-macroglobulin binding of proteases would help preserve the enzymatic activity of immobilized enzymes, binding to proteases would decrease the efficacy of A1AT and $\alpha_2$-macroglobulin binding to other proteases over time. This bioreactor retains a substantial percentage of the original hrIAP, CD73, AOAH, and A1AT activities in the extracorporeal bioreactor for at least 2 months.

EXAMPLE 8

In one example embodiment, treatment of a patient is accomplished with a bioreactor comprising an indwelling blood treatment device containing two polyether sulfone hollow fiber bundles in series in an indwelling catheter. 1,000 U apyrase, 500 U human CD73, and 2,000 U AOAH are co-immobilized on the first polyether sulfone hollow-fiber bundle, 32 mm long and 20 mm wide, within a polyurethane II catheter 21 mm wide and 70 mm long, and 10 µg of tissue plasminogen activator inhibitor (PAI-1) and 1 mg of $\alpha_2$-macroglobulin are co-immobilized on the second polyether sulfone hollow fiber bundle, 32 mm long and 20 mm wide, within the same polyurethane II catheter. After the immobilization procedures are completed, the bioreactor containing the first and second hollow fiber bundles in series in the catheter is placed in a paper or plastic container, which is sealed and sterilized by a dose of 25 kGy ionizing radiation so that the blood treatment device may be used immediately or stored in a refrigerator at 4° C. for several months prior to use. The blood treatment device is aseptically removed from the container at the time of surgical implantation.

The sterile bioreactor with 1,000 U apyrase, 500 U human CD73, and 2,000 U of AOAH immobilized on the first hollow fiber bundle and 10 µg PAI-1 and 1 mg $\alpha_2$-macroglobulin immobilized on the second hollow fiber bundle and connected in series in polyurethane II tubing, may be surgically implanted into the right femoral artery of a patient shortly after determination that this patient has sepsis to irreversibly dephosphorylate LPS, flagellin, extracellular nucleotides including DNA and RNA, and proinflammatory nucleoside triphosphates including eATP in the bloodstream of the patient to enable in vivo conversion of eATP to adenosine, irreversible deacylation of LPS to deacylated LPS (dLPS), PAI-1 inhibition of plasminogen activation by tissue plasminogen activator (tPA) and urokinase plasminogen activator (uPA) to prevent plasmin formation, and $\alpha_2$-macroglobulin inhibition of proteases that may destroy the immobilized enzymes. PAI-1 inhibition of tPA and uPA and $\alpha_2$-macroglobulin binding of proteases would help preserve the enzymatic activity of immobilized enzymes; however, binding to proteases would decrease the efficacy of PAI-1 and $\alpha_2$-macroglobulin binding to other proteases over time. This bioreactor retains a substantial percentage of the original apyrase, CD73, AOAH and PAI-1 activities in the bioreactors for about 2 months.

EXAMPLE 9

In one example embodiment, a bioreactor comprises a titanium oxynitride-coated stainless steel stent 80 mm long and 11 mm wide containing a polyvinylidene fluoride (PVDF) hollow fiber bundle 70 mm long and 10 mm wide, with 1,000 U human CD39/apyrase, 1,000 U CD73, and 50 µg lipopolysaccharide binding protein (LBP) co-immobilized on the surfaces of the PVDF hollow fiber bundle in the stent. After immobilization is completed, the stent is placed in a paper or plastic container, which is sealed and sterilized by a dose of 25 kGy ionizing radiation so that it may be used immediately or stored in a refrigerator at 4° C. for several months prior to use. The stent is aseptically removed from the container at the time of surgical implantation.

This bioreactor comprised of a sterile titanium oxynitride-coated stainless steel stent with 1,000 U human CD39/apyrase, 1000 U CD73, and 50 µg LPB co-immobilized on the surfaces of a PVDF hollow fiber bundle may be surgically implanted into the left femoral artery of a patient with COVID-19 infection and sepsis after admission into a hospital intensive care unit (ICU) for prophylactic treatment to destroy proinflammatory compounds including eATP, eADP, eDNA, and eRNA released into the bloodstream from damaged tissues and eRNA from the SARS-CoV2 virus. The CD39/apyrase and CD73 in the bioreactor irreversibly dephosphorylates approximately 10% of the LPS, extracellular nucleotides including eDNA and eRNA, and triphosphate nucleosides including eATP in the blood of a patient each hour in vivo as the blood passes through this bioreactor, including formation of adenosine from eATP. Although immobilized LPB binding of LPS would decrease the number of LPB attachment sites over time, this bioreactor may retain greater than 50% of the original CD39/apyrase, CD73 and LPB activity while implanted in the patient for at least one month.

EXAMPLE 10

In one example embodiment, treatment of a patient is accomplished with an extracorporeal blood treatment device consisting of two hollow fiber bundles in series. The first bioreactor is comprised of a polyether sulfone hollow fiber bundle 32 mm long and 20 mm wide in which 500 U apyrase, 100 U human CD73, and 500 U AOAH are co-immobilized, and the second bioreactor is comprised of a cellulose triacetate hollow fiber bundle 32 mm long and 20 mm wide in which 1 mg of A1AT and 1 mg of lipopolysaccharide binding protein (LBP) are co-immobilized. After immobilization, the first hollow fiber bundle and the second hollow fiber bundle are arranged in series in polyurethane II tubing 21 mm wide and 70 mm long. Then, this blood treatment device is placed in a paper or plastic container, which is sealed and sterilized by a dose of 25 kGy ionizing radiation so that this device may be used immediately or stored in a refrigerator at 4° C. for several months prior to use. This blood treatment device is aseptically removed from the container at the time of use.

The sterile blood treatment device with 500 U apyrase, 100 U human CD73, and 500 U of AOAH co-immobilized in the first hollow fiber bundle and 1 mg A1AT and 1 mg LBP co-immobilized on the interior surfaces of the second hollow fiber bundle may be connected to a vein of the right forearm of a patient shortly after determination that this patient has an abscess and sepsis. Although the binding of LPS by immobilized LBP would decrease the LBP available for additional binding over time and the binding of serine proteases by immobilized A1AT would decrease the A1AT available for additional binding of proteases over time, this extracorporeal bioreactor would retain a substantial percentage of the original apyrase, CD73, and AOAH activities for at least 2 months.

EXAMPLE 11

In one example embodiment, treatment of a patient is accomplished with an extracorporeal bioreactor comprised of a Fresenius Optiflux® F180NR dialyzer containing a polysulfone hollow fiber bundle with a surface area of 1.6 to 2.0 m². 2,000 hrIAP, 1,000 U human CD73, 2,000 U AOAH, 50 µg A1AT and 10 µg $\alpha_2$-macroglobulin are co-immobilized on the Optiflux® hollow fiber bundle. After the immobilization procedures are completed, the bioreactor is placed in a paper or plastic container, which is sealed and sterilized by a dose of 25 kGy ionizing radiation so that this blood treatment device may be used immediately or stored in a refrigerator at 4° C. for several months prior to use. The blood treatment device is aseptically removed from the container at the time it is connected to the patient.

The sterile Fresenius Optiflux® dialyzer bioreactor with 2,000 U hrIAP, 1,000 U human CD73, 2,000 U of AOAH, 50 µg A1AT and 10 µg of $\alpha_2$-macroglobulin co-immobilized on the interior surfaces of the hollow fiber bundle in this bioreactor is connected to a vein in the patient's right forearm, with blood transfer lines leading from the patient to a peristaltic pump, to the Optiflux® bioreactor, and back to a vein in the patient's right forearm shortly after determination that this patient has bacteremia, which is caused by a drug resistant strain of *Klebsiella oxytoca*, to prevent the development of sepsis. Although the A1AT and $\alpha_2$-macroglobulin binding of proteases would help preserve the enzymatic activity of immobilized enzymes, binding to proteases would decrease the efficacy of A1AT and $\alpha_2$-macroglobulin binding to other proteases in the bloodstream over time. This bioreactor retains a substantial percentage of the original hrIAP, CD73, and AOAH activities for at least 1 month. This example illustrates how enzymes may be immobilized in kidney dialysis assemblies which then can be sterilized and used to treat blood of a patient for sepsis and other medical conditions.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

The invention claimed is:

1. A blood treatment method, comprising:
   inducing flow of blood of a human or animal patient through a blood treatment device inlet and outlet; and
   detoxifying at least one biological agent contained within the blood by passing the blood over at least one bioreactor surface having attached a phosphatase enzyme and/or an acyloxyacyl hydrolase (AOAH) enzyme, with the at least one bioreactor surface being contained within the blood treatment device and wherein the at least one biological agent is selected from the group consisting of:
   Gram negative bacterial lipopolysaccharide (LPS);
   Gram negative bacterial flagellin;
   Gram positive bacterial lipoteichoic acid;
   Gram positive bacterial flagellin;
   one or more bacterial extracellular nucleoside triphosphates including adenosine triphosphate (ATP), nucleoside diphosphates including adenosine diphosphate (ADP), and nucleotides including deoxyribonucleic acid (DNA) and ribonucleic acid (RNA);
   one or more yeast extracellular nucleoside triphosphates including ATP, nucleoside diphosphates including ADP, and nucleotides including DNA and RNA;
   one or more fungal extracellular nucleoside triphosphates including ATP, nucleoside diphosphates including ADP, and nucleotides including DNA and RNA;
   one or more viral extracellular nucleotides including DNA and RNA; and
   one or more host extracellular nucleoside triphosphates including ATP, nucleoside diphosphates including ADP, and nucleotides including DNA and RNA, and combinations thereof, wherein the blood treatment device includes a bioreactor associated with the bioreactor surface, and wherein the bioreactor comprises at least one of one or more surfaces of a hollow fiber bundle in a stent.

2. The blood treatment method of claim 1, wherein the hollow fiber bundle comprises 400 to 20,000 biocompatible hollow fibers made from polysulfone, wherein the hollow fibers have an internal diameter of 50 to 500 µm, a wall thickness of 10 to 50 µm, and a length of 3 to 50 cm, and wherein the hollow fibers are arranged in parallel in the hollow fiber bundle.

3. The blood treatment method of claim 1, wherein the phosphatase enzyme includes one or more human phosphatase enzymes including any combination of alkaline phosphatase (AP), apyrase/cluster of differentiation 39 (CD39; ecto-apyrase), and cluster of differentiation CD73 (CD73; ecto-5'-nucleotidase).

4. The blood treatment method of claim 1, wherein the acyloxyacyl hydrolase (AOAH) enzyme comprises human AOAH from human blood or tissues or synthetic human AOAH from recombinant deoxyribonucleic acid (DNA) technology.

5. The blood treatment method of claim 1, further comprising connecting the blood treatment device inlet and outlet to the patient.

6. The blood treatment method of claim 1, further comprising treating the blood continuously.

7. The blood treatment method of claim 1, further comprising circulating the blood through one or more indwelling stents and catheters by a blood pressure created by a beating heart of the patient.

8. The blood treatment method of claim 1, wherein phosphatase enzymes including, but not limited to alkaline phosphatase (AP), intestinal alkaline phosphatase (IAP), *Saccharomyces boulardii* AP (SBAP), apyrase, apyrase/cluster of differentiation 39 (CD39; ecto-apyrase), and cluster of differentiation 73 (CD73; ecto-5'-nucleotidase) irreversibly detoxify the at least one biological agent contained within the blood by dephosphorylation.

9. The blood treatment method of claim 1, wherein the AOAH enzyme detoxifies the at least one biological agent contained within the blood by deacylation.

10. The blood treatment method of claim 1, wherein one or more enzymes including alkaline phosphatase (AP), *Saccharomyces boulardii* AP (SBAP), apyrase, apyrase/cluster of differentiation 39 (CD39; ecto-apyrase), cluster of differentiation 73 (CD73; ecto-5'-nucleotidase), and AOAH enzymes are covalently attached to the bioreactor surface.

11. The blood treatment method of claim 1, wherein detoxifying the at least one biological agent contained within the blood of the patient therapeutically treats at least one of sepsis, septic shock, inflammation, bacteremia, bacterial infections, yeast infections, fungal infections, viral infections, systemic inflammatory response syndrome (SIRS), Gram negative bacterial lipopolysaccharide (LPS) in patient blood, Gram positive bacterial lipoteichoic acid in the blood, inflammatory bowel disease (IBD), inflammatory bowel syndrome (IBS), Crohn's disease, ulcerative colitis, enterocolitis, necrotizing enterocolitis (NEC), meningitis, meningococcemia, trauma or hemorrhagic shock, burns, liver disease, pancreatitis, periodontal disease, pneumonia, cystic fibrosis, asthma, alpha-1 antitrypsin (A1AT) deficiency, chronic obstructive pulmonary disease (COPD), pulmonary fibrosis, tuberculosis, coronary heart disease, congestive heart failure, infectious endocarditis, renal disease, hemolytic uremic syndrome, kidney disease, autoimmune diseases including rheumatoid arthritis, systemic lupus erythematosus, mast cell activation disorders, cancer, diabetes, infection resulting in LPS or lipoteichoic acid in patient blood, abscesses resulting in LPS or lipoteichoic acid in patient blood, protein aggregation disorders including neurodegenerative diseases, Alzheimer's disease, Parkinson's disease, Huntington's chorea, macular degeneration, amyloidosis, and amyotrophic lateral sclerosis, arthritis, atherosclerosis, aging, cancer, diabetes, obesity, emotional stress, anxiety, and patients undergoing surgery, chemotherapy and transplants.

12. The blood treatment method of claim 1, wherein the at least one bioreactor surface is provided with continuous flow of the blood that continues until the at least one biological agent being detoxified has each been reduced to predetermined levels.

13. The blood treatment method of claim 1, wherein an immobilized anti-protease plasma protein comprising $\alpha_2$-macroglobulin is used singly or in combination with one or more immobilized alkaline phosphatase (AP) and AOAH enzymes in the at least one bioreactor surface to reduce proteolytic destruction of the immobilized enzymes, to maintain activity of the enzymes in the bioreactor, and to reduce tissue destruction and inflammation caused by proteases in the bloodstream.

14. The blood treatment method of claim 1, wherein the phosphatase and AOAH enzymes are immobilized and are used to remove selected LPS and proinflammatory compounds within a biological system, including but not limited to those produced by microorganisms including bacteria, yeast, fungi, viruses and infected or damaged host tissues in humans and animals, and more specifically, to remove LPS, lipoteichoic acid, flagellin, and microbial or host extracellular ATP, ADP, DNA, and RNA in a bloodstream of the patient by passage of the blood over the bioreactor surface in a blood treatment device without adding any chemicals to the blood of the patient for continuous treatment until the LPS and proinflammatory compounds have been reduced to predetermined levels.

15. The blood treatment method of claim 1, further comprising surgically implanting an indwelling bioreactor into a patient to enable blood of the patient to flow in the following way:
from a first vein through an inlet associated with the indwelling bioreactor and an outlet associated with the bioreactor in fluid connection to the first vein of the patient.

16. The blood treatment method of claim 1, wherein the dephosphorylation of extracellular ATP to adenosine monophosphate (AMP) plus phosphate by the combined action of immobilized alkaline phosphatase (AP) and the action of cluster of differentiation CD73 (CD73; ecto-5'-nucleotidase) on the endothelial surfaces of blood vessels and tissue cells of a patient results in an in vivo conversion of ATP into adenosine which inhibits inflammation without adding chemicals to the bloodstream of the patient.

17. The blood treatment method of claim 1, wherein immobilized AOAH on the at least one bioreactor surface enables in vivo conversion of proinflammatory LPS to deacylated LPS (dLPS), a competitive inhibitor of LPS for cellular attachment sites, so that dLPS inhibits inflammation caused by LPS without adding chemicals to the bloodstream of the patient.

* * * * *

UNITED STATES PATENT AND TRADEMARK OFFICE
CERTIFICATE OF CORRECTION

| | | |
|---|---|---|
| PATENT NO. | : 12,070,543 B2 | Page 1 of 1 |
| APPLICATION NO. | : 18/323055 | |
| DATED | : August 27, 2024 | |
| INVENTOR(S) | : Donald S. Orth | |

It is certified that error appears in the above-identified patent and that said Letters Patent is hereby corrected as shown below:

In the Specification

In Column 9, Line 64, "TAP" should be "IAP".

Signed and Sealed this
Twenty-fifth Day of February, 2025

Coke Morgan Stewart
*Acting Director of the United States Patent and Trademark Office*